US009320789B2

(12) United States Patent
Venkatesan et al.

(10) Patent No.: US 9,320,789 B2
(45) Date of Patent: Apr. 26, 2016

(54) COMBINATIONS OF GENE DELETIONS FOR LIVE ATTENUATED SHIGELLA VACCINE STRAINS

(71) Applicant: United States Army, Fort Detrick, MD (US)

(72) Inventors: Malabi Venkatesan, Bethesda, MD (US); Ryan Ranallo, Gaithersburg, MD (US); Shoshana Barnoy, Rockville, MD (US)

(73) Assignee: The United States of America as represented by the Secretary of the Army, on behalf of the Walter Reed Army Institute of Research, Washington, DC (US)

(*) Notice: Subject to any disclaimer, the term of this patent is extended or adjusted under 35 U.S.C. 154(b) by 0 days.

(21) Appl. No.: 14/628,842

(22) Filed: Feb. 23, 2015

(65) Prior Publication Data

US 2015/0165012 A1 Jun. 18, 2015

Related U.S. Application Data

(62) Division of application No. 12/149,076, filed on Apr. 25, 2008, now Pat. No. 8,986,708.

(60) Provisional application No. 60/907,974, filed on Apr. 25, 2007.

(51) Int. Cl.
| | |
|---|---|
| *A01N 63/00* | (2006.01) |
| *A01N 65/00* | (2009.01) |
| *C12P 1/00* | (2006.01) |
| *C12N 1/00* | (2006.01) |
| *A61K 39/112* | (2006.01) |
| *A61K 39/00* | (2006.01) |

(52) U.S. Cl.
CPC ....... *A61K 39/0283* (2013.01); *A61K 2039/522* (2013.01)

(58) Field of Classification Search
CPC ........... A61K 39/0283; A61K 35/3574; A61K 2039/51; A61K 2039/52; A61K 2039/522; C12N 5/70
See application file for complete search history.

(56) References Cited

U.S. PATENT DOCUMENTS

| | | |
|---|---|---|
| 5,589,380 A | 12/1996 | Fasano et al. |
| 6,759,241 B1 | 7/2004 | Hone et al. |

OTHER PUBLICATIONS

Ranallo (ICSS. International Research in Infectious Diseases. 2006 Annual Meeting Presentation).*
Venkatesan et al., (Infection and Immunity. 2002. vol. 70(6): 2950-2958).*
Kotloff et al., (Infection and Immunity. 2000. vol. 68(3): 1034-1039).*
Kotloff et al., (J. Infect. Dis. 2004. vol. 190(10): 1745-1754).*
Kotloff et al, "Shigella flexneri 2a strain CVD 1207, with specific deletions in virG, sen, set, and guaBA, is highly attenuated in humans", Mar. 1, 2000, pp. 1034-1039, vol. 68, No. 3, Publisher: Infection and Immunity.
Collins et al., "Safety and colonization of two novel virG(icsA)-based live Shigella sonnei vaccine strains in rhesus macaques (Macaca mulatta)", 2008, pp. 88-94, vol. 58, No. 1, Publisher: Comparative Medicine (MEMPHIS).
International Preliminary Report on Patentability issued in corresponding International Application No. PCT/US2008/005342 dated Oct. 27, 2009,.
Katz et al., "2 Studies Evaluating the Safety and Immunogenicity of a Live, Attenuated Shigella flexneri 2a Vaccine (SC602) and Excretion of Vaccine Organisms in . . . ", 2004, pp. 923-930, vol. 72, No. 2, Publisher: Infection and Immunity.
Kotloff et al., "Deletion in the Shigella Endotoxin Genes Further Attenuates Shigella flexneri 2a Bearing Guanine Auxotrophy in Phase 1 Trial of CVD 1204 and CVD 1208", 2004, vol. 190, No. 10, Publisher: J. Infect. Dis.
Ranallo, "Annual Meeting Presentation", 2006, Publisher: ICSS. International Research in Infectious Diseases.
Ranallo et al., "Immunogenicity and characterization of WRSF2G 11: A second generation live attenuated Shigella flexneri 2a vaccine strain", 2007, pp. 2269-2278, vol. 25, Publisher: Vaccine.
Ranallo et al., "Developing live Shigella vaccines using λ Red recombineering", 2006, pp. 462-469, vol. 47, Publisher: FEMS Immunol. Med Microbiol.
Venkatesan and Ranallo, "Live-attenuated Shigella vaccines", 2006, pp. 669-686, vol. 5, No. 5, Publisher: Expert Rev. Vaccines.
Venkatesan et al., "Construction characterization, and animal testing of WRSd1, a Shigella dysenteriae 1 vaccine", 2002, pp. 2950-2958, vol. 70, No. 6, Publisher: Infection and Immunity.

* cited by examiner

*Primary Examiner* — Ja'Na Hines
(74) *Attorney, Agent, or Firm* — Elizabeth Arwine

(57) ABSTRACT

*Shigella* vaccine strains whose primary attenuating feature is deletion of the virG(icsA) gene and additional two or more deletions in setAB(shET1), senA(shET2), senB(shET2-2), stxAB, and msbB2 genes. Thus, the vaccine strain will have three or more deletions in the identified genes, will be safer, and will reduce or eliminate symptoms of fever and diarrhea in humans. The following specific vaccine strains have been constructed: WRSS3 (ΔsenA, ΔsenB, ΔvirG, ΔmsbB2), WRSf2G15 (ΔvirG, ΔsetAB, ΔsenA, ΔsenB, ΔmsbB2), and WRSd5 (ΔvirG, ΔstxAB, ΔsenA, ΔsenB, ΔmsbB2).

16 Claims, 12 Drawing Sheets

MOSELY (*S. sonnei*)
0749 tet<sup>R</sup>
PRODUCTION CELL BANK

⇩ -- RECOMBINEERING
⇩ -- TET-RESISTANCE
     ELIMINATION
⬇ -- ALLELIC EXCHANGE

ΔsenA tet<sup>R</sup>          ΔvirG tet<sup>R</sup>

ΔsenA, ΔsenB tet<sup>R</sup>    WRSS1 (ΔvirG)

ΔsenA, ΔsenB, ΔvirG tet<sup>R</sup>

WRSS2 (ΔsenA, ΔsenB, ΔvirG)

WRSS3 (ΔsenA, ΔsenB, ΔvirG, ΔmsbB2)

CONSTRUCTION OF SHIGELLA VACCINE STRAINS
WRSS1, WRSS2, AND WRSS3 VIA *S. Sonnei* STRAIN (MOSELY 0749)
THAT IS STABLE FOR THE VIRULENCE PHENOTYPE.

FIG. 1

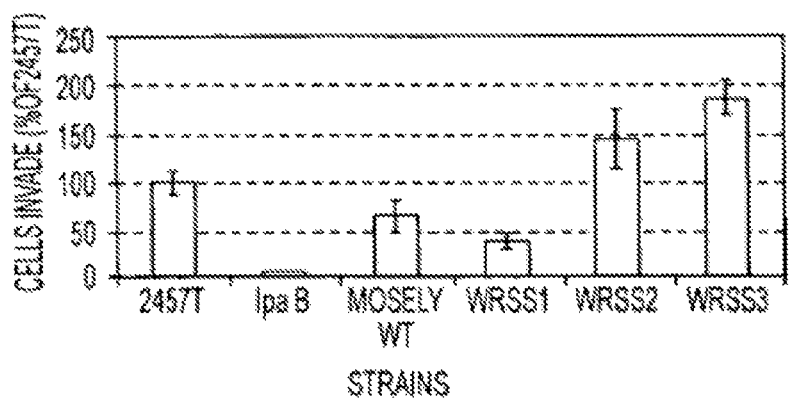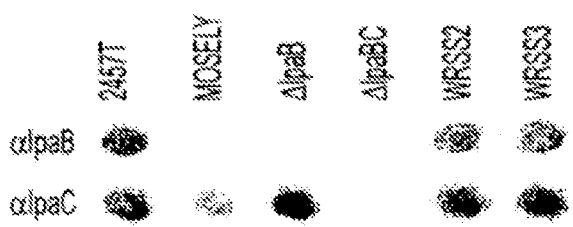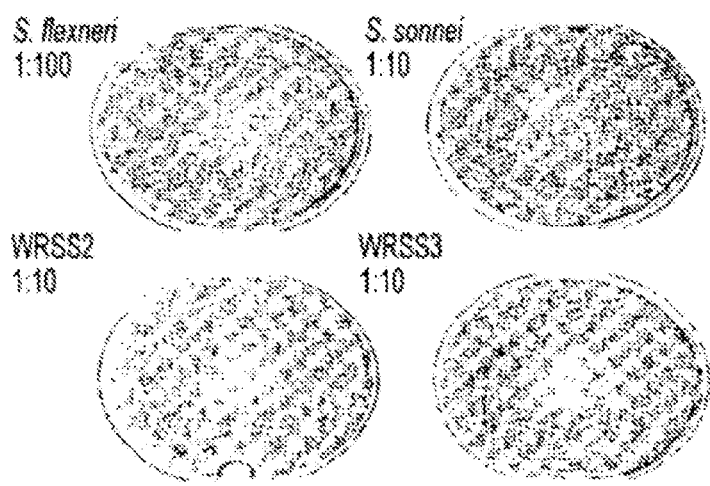
CHARACTERIZATION OF THE S. sonnei VACCINE STRAINS VIA HeLa CELL INVASION ASSAY (A), COLONY IMMUNOBLOTING (B), AND PLAQUE ASSAY (C).
FIG. 2

| GROUP (# GUINEA PIGS) | VACCINE STRAIN | DOSE | ROUTE |
|---|---|---|---|
| 1 (10) | NAIVE | NA | OC |
| 2 (10) | WRSS1 | $4 \times 10^8$ | OC |
| 3 (10) | WRSS2 | $4 \times 10^8$ | OC |
| 4 (10) | WRSS3 | $4 \times 10^8$ | OC |

MASTER

D0 — IMMUNIZE BLOOD MUCOSAL
D14 — IMMUNIZE BLOOD, MUCOSAL
D28 — BLOOD, MUCOSAL
D41 — CHALLENGE
D55 — BLOOD

GUINEA PIG OCULAR (OC) IMMUNIZATION PROTOCOL

FIG. 3

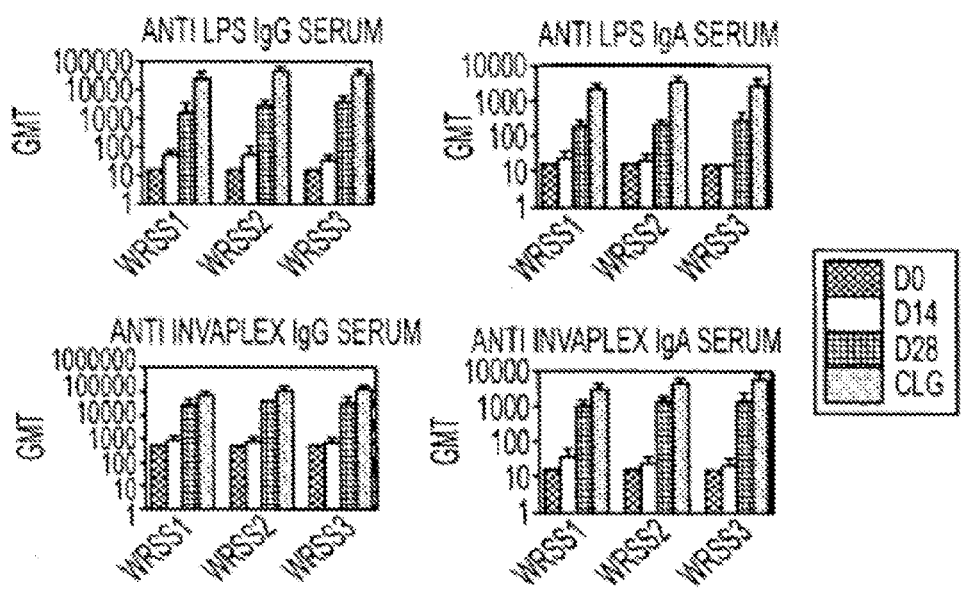
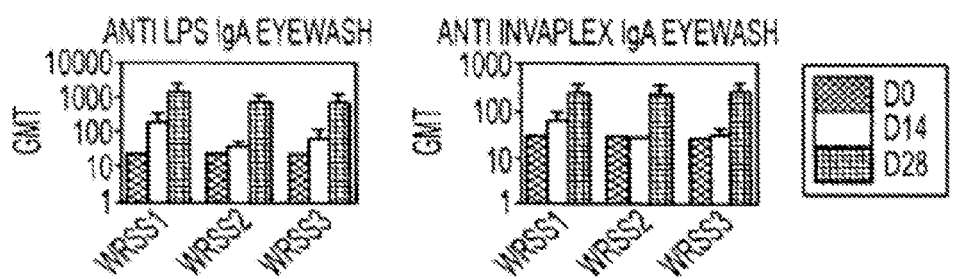
SERUM AND MUCOSAL ANTIBODY
TITERS IN OCCULARLY IMMUNIZED GUINEA PIGS.
FIG. 4

PROTECTIVE EFFICACY OF WRSS1, WRSS2, AND WRSS3
FOLLOWING CHALLENGE WITH WILD-TYPE S. sonnei ST

|  | MONKEY ID | PRE- | DAY OF STUDY | | | | | | | |
|---|---|---|---|---|---|---|---|---|---|---|
|  |  |  | 1 | 2 | 3 | 4 | 5 | 6 | 7 | 10 |
| WRSS1 | F942 | - | + | + | - | + | - | - | - | - |
|  | JKA | - | + | + | + | + | + | + | - | - |
|  | JPT | - | + | + | + | - | - | + | - | - |
|  | TAB | - | + | + | + | + | + | + | + | - |
|  | B34Z | - | + | - | - | - | - | - | - | - |
| WRSS2 | 2OH | - | + | - | - | - | - | - | - | - |
|  | CJZW | - | - | - | - | - | - | - | - | - |
|  | 694Z | - | + | + | + | + | + | + | + | - |
|  | C4ZZ | - | - | - | - | - | - | - | - | - |
|  | 89-129 | - | + | - | + | - | - | - | - | - |
| WRSS3 | J778 | - | + | + | + | + | + | - | - | - |
|  | 89-155 | - | + | + | + | + | - | - | - | - |
|  | A14Z | - | + | + | - | - | - | - | - | - |
|  | BVF | - | + | + | - | - | + | - | - | - |
|  | TAJ | - | + | + | - | - | - | - | - | - |

WRSS1: ΔvirG
WRSS2: ΔvirG, ΔshET2, ΔshET2-2
WRSS3: ΔvirG, ΔshET2, ΔshET2-2, ΔmsbB2

VACCINE EXCRETION OF WRSS1, WRSS2, AND WRSS3 IN MONKEY IMMUNIZATION PROTOCOL.

FIG. 7

CONSTRUCTION OF S. flexneri 2a VACCINE DERIVATIVES

```
              ┌─────────────────────┐
              │       2457T         │
              │ (PRODUCTION CELL BANK)│
              └──────────┬──────────┘
                         ↓
              ┌─────────────────────┐
              │   WRSf2G(ΔvirG)     │
              └──────────┬──────────┘
                         ↓
              ┌─────────────────────┐
              │ WRSf2G10(ΔvirG, ΔsenA)│
              └──────────┬──────────┘
                         ↓
Heterologous Antigen Carrier Strain
┌──────────────────┐   ┌─────────────────────────┐   ┌──────────────────────────┐
│ WRSf2G13(ΔvirG,  │ ← │ WRSfG11(ΔvirG, ΔsenA,   │ → │ WRSf2G14(ΔvirG, ΔsenA,   │
│ ΔsenA, Δset,Δasd)│   │       Δset)             │   │   Δset, ΔmsbB2)          │
└──────────────────┘   └───────────┬─────────────┘   └────────────┬─────────────┘
 Ranallo et. al.,       Ranallo et. al., Vaccine 2007              ↓
 Vaccine 2007                        ↓
                       ┌─────────────────────────┐   ┌──────────────────────────┐
                       │ WRSfG12(ΔvirG, ΔsenA,   │   │ WRSf2G15(ΔvirG, ΔsenA,   │
                       │   ΔsetAB, ΔsenB)        │   │ Δset, ΔmsbB2, ΔsenB)     │
                       └─────────────────────────┘   └──────────────────────────┘
```

CONSTRUCTION OF SHIGELLA VACCINE STRAINS
WRSf2G12 AND WRSf2G15 VIA S. flexneri STRAIN 2457T.

FIG. 8

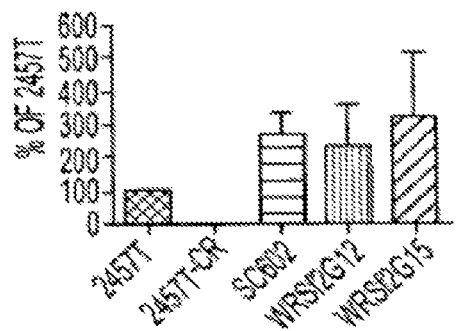
CHARACTERIZATION OF THE WRSf2G12 AND WRSf2G15 VACCINE STRAINS VIA COLONY IMMUNOBLOTTING (A) AND HeLa CELL INVASION ASSAY (B).
FIG. 9

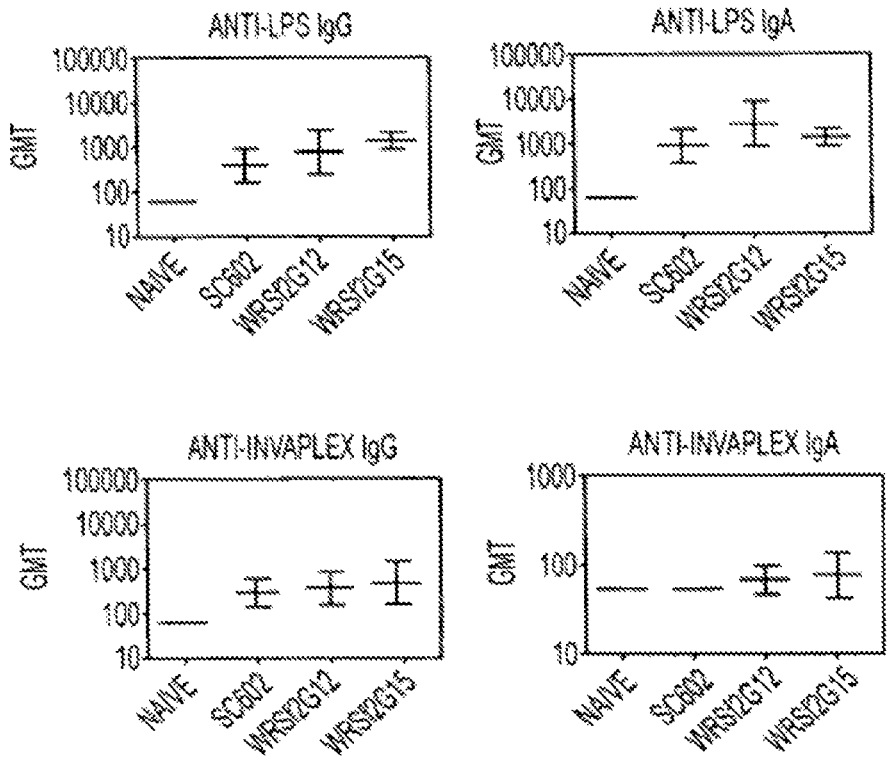
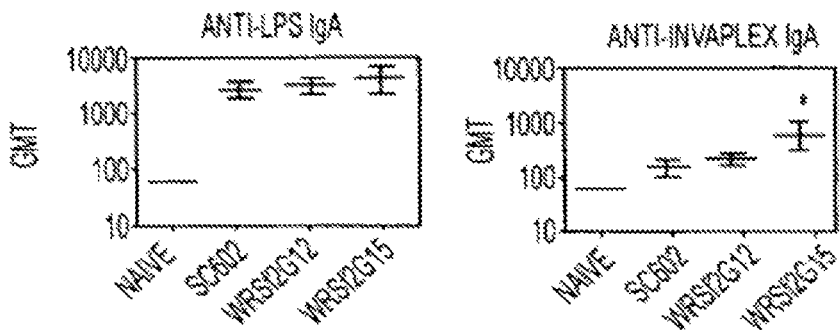
FIG. 11

PROTECTIVE EFFICACY OF SC602, WRSf2G12, AND WRSf2G15 FOLLOWING CHALLENGE WITH WILD-TYPE S. flexneri STRAIN 2457T.

COMBINATIONS OF GENE DELETIONS FOR LIVE ATTENUATED SHIGELLA VACCINE STRAINS

BACKGROUND OF THE INVENTION

1. Field of the Invention

The present invention relates generally to *Shigella* vaccine, strains, their use in vaccines, and the methods for treatment of dysentery.

2. Related Art

*Shigella* spp. is the causative agent of bacillary dysentery. The distal end of the colon and the rectum, which show intense and acute mucosal inflation, are the areas of the gastrointestinal (GIT) moat most affected during shigellosis. A very low inoculum of 10-100 bacteria is sufficient to cause the disease, which then spreads easily, often directly, by the fecal-oral route or by flies contaminating food and water. Appropriate antibiotics, such as those effective against gram-negative bacteria, are used to combat *Shigella* infection; however, as with most bacterial pathogens, an increase in antibiotic resistance has dramatically emphasized the need for a safe and effective vaccine.

Recent *Shigella* vaccine candidates include subcellular complexes purified from virulent cultures (e.g., Invaplex vaccine) that encompass detoxified lipopolysaccharide (LPS) conjugated to carrier proteins and live attenuated vaccine strains. Attempts to utilize whole-cell inactivated organisms that are given in high and multiple doses have met with poor immunogenicity and protective efficacy. Live vaccines appear to offer a better approach since they mimic natural infection while subverting the clinical outcome.

U.S. Pat. No. 5,762,941 illustrates one live vaccine approach and involves the loss of virG(icsA) gene in *S. flexneri* 2a, *S. sonnei*, and *S. dysenteriae* 1. Vaccine strains SC602, WRSS1, and WRSd1 resulted, of which SC602 and WRSS1 were tested in Phase 1 trials on human volunteers and found to be safe at oral doses ranging from $10^3$ to $10^4$ CFU. However, 15-25% of the volunteers administered SC602 or WRSS1 showed symptoms of mild diarrhea and fever.

U.S. Pat. No. 5,589,380 and U.S. Pat. No. 5,468,639 illustrate another approach, whereby two candidate genes, setAB (shET1) and senA(shET2), are utilized since they have previously been shown to encode enterotoxic activity. While setAB(shET1) is present predominantly on the chromosome of *S. flexneri* 2a strains, the senA(shET2) gene is located on the large virulence plasmid of all *Shigella* strains.

An article in the Journal of Infectious Disease 2004, 190: 1745-54 illustrates a still further approach to achieve a live *Shigella* vaccine. The symptoms of diarrhea and fever seen with a guaBA mutant of *S. flexneri* 2a vaccine candidate CVD1204 were ameliorated with the administration of CVD1208, which contains the guaBA mutation in combination with deletions in setAB and senA(shET2) genes. Notably, senB(shET2-2) constitutes a putative enterotoxin gene that shares >60% homology at the amino acid level with senA(shET2-1) and could be a functional analog of senA (shET2). Although highly attenuated, CVD1208 is given at very high doses ($10^9$) which can induce fever in 10% of subjects.

U.S. Pat. No. 6,759,241 is directed towards an approach involving the msbB2 gene in live vaccine development. The msbB2 gene encodes a fatty acyl transferase enzyme that adds fatty acid residues to the lipid A portion of the bacterial LPS molecule. The lipid A portion constitutes an endotoxin that is responsible for the potent inflammatory activity and pyrogenic properties of bacterial LPS. In an *E. coli* background, a mutation in the msbB gene results in a less toxic LPS but, unlike *E. coli*, *Shigella* has two msbB genes, the first (msbB1) on the chromosome and the second (msbB2) on the virulence plasmid. Deletion of either msbB gene in a *S. flexneri* 2a background results in reduced histopathology of *Shigella* infection in the rabbit ileal loop model and deletion of both msbB genes reduces the pathology even further.

Data from our lab, which was presented at the Gordon Conference in 2006, indicates that loss of both msbB1 and msbB2 genes in a *S. flexneri* 2a background affects the growth and invasive properties of the bacteria. However, loss of msbB1 or msbB2 gene alone does not compromise the growth, invasiveness, immunogenicity, or the protection generated in an animal model of *Shigella* infection when compared to infection with the wild-type *Shigella* strain. Furthermore, loss of either msbB gene resulted in lower levels of proinflammatory cytokines (e.g., IL-1b and MCP-1) in lung washes of mice intranasally infected with the bacteria.

A review article in Expert Review Vaccines 2006, 5:5 discusses several live-attenuated *Shigella* vaccines with well-defined mutations in specific genes. In these studies, the immune responses obtained with each vaccine strain were compared with data obtained from challenge trials using wild-type *Shigella* strains. The data from these trials indicated that live attenuated vaccine strains elicited immune responses comparable to individuals challenged with wild-type *Shigella* strains. Thus, the combination of gene deletions is expected to eliminate reactogenicity while inducing protective immune responses.

An article appearing in Vaccine 2007, 25: 2269-2278 describes a *S. Flexneri* 2a vaccine candidate, WRSf2G11, that has deletions in the virG(icsA), set, and sen genes. This strain was constructed using the lambda red recombinase system and demonstrated that virG-based *Shigella* vaccine strains lacking enterotoxin genes show lower levels of reactogenicity without hampering robust immune responses.

SUMMARY OF THE INVENTION

The invention relates to *Shigella* vaccine candidates of all 4 major serotypes whose primary attenuating feature is deletion of the virG(icsA) gene and additional deletions in two or more of setAB(shET1), senA(shET2), senB(shET2-2), stxAB, and msbB2 genes. Thus, the strain will have three or more deletions in the identified genes and will be safer, resulting in the absence of or reduced fever and diarrhea when tested in human volunteers.

The following vaccine strains have been constructed: WRSS3 (ΔsenA, ΔsenB, ΔvirG, ΔmsbB2), WRSf2G15 (ΔvirG, ΔsetAB, ΔsenA, ΔsenB, ΔmsbB2), and WRSd5 (ΔvirG, ΔstxAB, ΔsenA, ΔsenB, ΔmsbB2).

The strains of the invention are designed to protect against dysentery and diarrhea caused by *Shigella flexneri*, *Shigella sonnei*, *Shigella dysenteriae*, and *Shigella boydii*. In addition, the strains of the invention can be used in mixtures of live attenuated polyvalent vaccines that contain two or more serotypes of *Shigella* (e.g., *Shigella flexneri* and *Shigella sonnei*). The strains of the invention can also be used in combination with live attenuated vaccines against enterotoxigenic *E. coli* (ETEC) to provide protection against dysentery and diarrhea caused by these bacteria. As is readily apparent, multivalent vaccines employing these strains can protect against the common serogroups of *Shigella* and ETEC.

Prime-boost, whereby initial immunization with a live vaccines is followed by immunization with a subunit vaccine, will provide protection against dysentery and diarrhea caused by *Shigella*.

The *Shigella* vaccine strains of the invention can be used as carriers of antigens from other diarrheal pathogens such as *Campylobacter*, mucosal delivery vectors for other prokaryotic antigens, vectors for eukaryotic antigens, and carriers of immune modulators such as cytokines.

The *Shigella* vaccine strains of the invention can be used at doses as low as $10^4$ to $10^6$ CFU. While virG(icsA)-based vaccines have been tested in humans and shown to be reasonably safe, 15-25% of the volunteers have shown reactogenic symptoms that are unacceptable. The deletion of the virG (icsA) gene combined with deletions of genes associated with enterotoxic activity, putative enterotoxins, and/or genes associated with LPS toxicity will create a safer oral *Shigella* vaccine.

The *Shigella* vaccine strains are characterized as having the virG(icsA) gene deletion/inactivation in combination with two or more of setAB(shET1), senA(shET2), senB(shET2-2), stxAB, and msbB2 genes. The *Shigella* vaccine is a non-virulent strain of 4 serogroups, namely *S. flexneri, S. sonnei, S. dysenteriae*, and *S. boydii*.

The *Shigella* vaccine strains are characterized by one or more of the following traits: invasiveness in epithelial cells, absence of plaques in epithelial cell monolayers, absence of keratoconjunctivitis induction in guinea pig eyes, induction of immune responses that are protective from challenge in guinea pigs, and efficient excretion from monkeys after a intragastric inoculation of $10^{10}$ CFU.

The *Shigella* vaccine strains can be formulated as an immunogenic composition wherein the strains are mixed with a pharmaceutically acceptable carrier and are present in an amount that induces a protective immune response after one or more administrations. The multistrain vaccine composition can be formulated as a single dose that achieves a protective immune response. The exact amount may be empirically determined and would be variable depending on animal type, weight, condition, and age.

The compositions and strains of the invention can be packaged as a kit to facilitate handling and provide optimal protection. The kit may comprise one or more containers, each of which contains a specific *Shigella* vaccine strain or mixture of strains. The amount or type of stains may be selected as part of a regimen or application. The *Shigella* vaccine strains of the invention can be packaged with written instructions and in a manner to preserve viability of the strains.

When administered to a subject in a single dose or series of doses, the *Shigella* vaccine strains of the invention induce a mucosal (oral or intranasal) immune response. One advantage of the vaccine formulation is that a protective response can be achieved in a single oral dose containing relatively few colony forming units ($10^4$ to $10^6$ CFU) compared to the alternatives of multiple doses of a live, noninvasive vaccine or inactivated whole cell vaccine strains.

Further features and advantages of the invention, as well as the structure and operation of its various embodiments, are described in detail below with reference to the accompanying drawings.

BRIEF DESCRIPTION OF THE DRAWINGS

The foregoing features and advantages of the invention will be apparent from the following, more particular description of a preferred embodiment of the invention, as illustrated in the accompanying drawings wherein like reference numbers generally indicate identical, functionally similar, and/or structurally similar elements. The left most digits in the corresponding reference number indicate the drawing in which an element first appears.

FIG. 1 shows the construction of specified *Shigella* vaccine strains, namely WRSS1, WRSS2, and WRSS3.

FIG. 2 shows characterization of the WRSS1, WRSS2, and WRSS3 vaccine strains via HeLa cell immunoassay (2A), colony immunoblotting (2B), and plaque assay (2C).

FIG. 3 shows the guinea pig immunization protocol for WRSS1, WRSS2, and WRSS3.

FIG. 4 shows serum antibody titers (4A) and mucosal antibody titers (4B) in occularly immunized guinea pigs.

FIG. 7 shows the vaccine excretion results for WRSS1, WRSS2, and WRSS3 in the monkey immunization protocol.

FIG. 8 shows the Construction of *Shigella* vaccine strains WRSf2G12 and WRSf2G15 via *S. flexneri* strain 2457T.

FIG. 9 shows the Characterization of the WRSf2G12 and WRSf2G15 vaccine strains via colony immunoblotting (A) and HeLa cell invasion assay (B).

FIG. 11 shows the Serum antibody titer (A) and mucosal (B) antibody titer in ocularly immunized guinea pigs.

DETAILED DESCRIPTION OF AN EXEMPLARY EMBODIMENT OF THE PRESENT INVENTION

Figure 5:
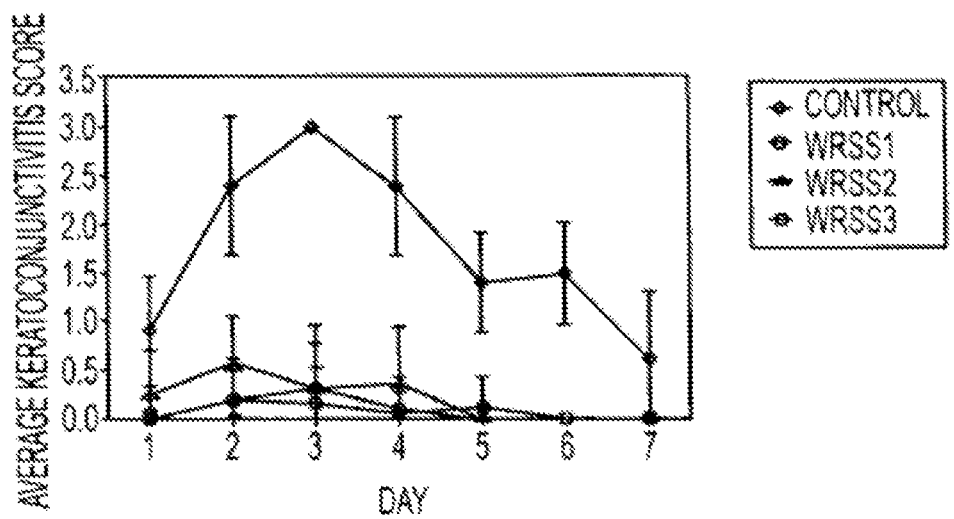
FIG. 5 shows the protective efficacy of WRSS1, WRSS2, and WRSS3 following a wild-type strain challenge.
Figure 6:
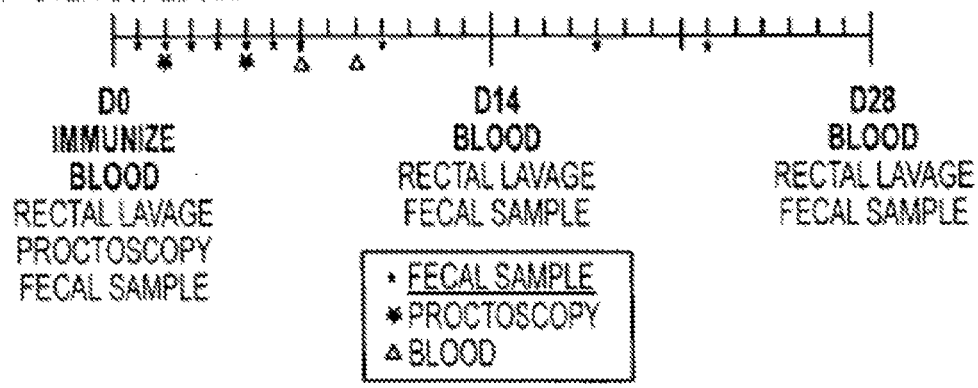
FIG. 6 shows the monkey intragastric immunization protocol.
Figure 10:
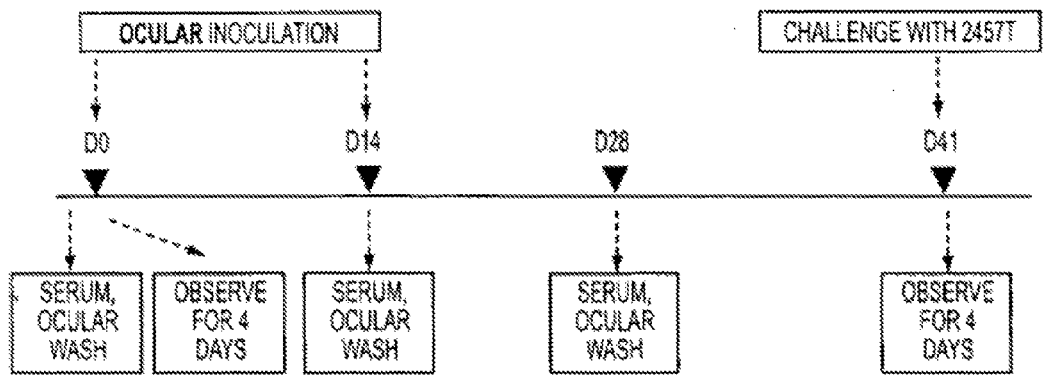
FIG. 10 shows the Guinea pig ocular (OC) immunization protocol.

A preferred embodiment of the invention is discussed in detail below; however, while specific exemplary embodiments are discussed, it should be understood that this is done for illustration purposes only. A person skilled in the relevant art will recognize that other components and configurations can be used without parting from the spirit and scope of the invention.

WRSS1, SC602, and WRSd1, which are the three *Shigella* vaccine candidates based on deletions of the virG(icsA) gene, have been recently tested in Phase 1 clinical trials on healthy adults, indicating that all three vaccines are safe when given orally in doses ranging from $10^3$ to $10^4$ CFU. Furthermore, volunteers vaccinated with SC602 were protected from severe dysentery following challenge with a homologous wild-type *S. flexneri* 2a strain. However, expanded phase 1 clinical trials revealed that an unacceptable number of the volunteers given SC602 or WRSS 1 had symptoms of mild diarrhea and fever. Recent clinical trials carried out by researchers at the Center for Vaccine Development (CVD) have indicated that most of these symptoms could be ameliorated by the removal of ShET1 (set) and ShET2-1 (senA) enterotoxins. An additional target for further attenuating live *Shigella* vaccines involves modification of lipid A, which is the bioactive center of LPS. Through deletion of a late acyltransferase (msbB), alterations to the canonical structure of lipid A have been shown to significantly reduce the endotoxicity of the molecule.

New, second-generation virG(icsA)-based *S. sonnei* vaccine candidates (WRSS2 and WRSS3) with additional deletions in two plasmid-borne enterotoxins and a lipid A modifying gene, which should reduce the reactogenic symptoms associated with WRSS1, have been constructed. Both WRSS2 (consisting of deletions in virG(icsA), ShET2-1 (senA), and ShET2-2 (senB)) and WRSS3 (consisting of deletions such as in WRSS2 with an additional deletion in the plasmid-borne msbB2 gene) are invasive in cultured epithelial cells but negative in plaque assays. Guinea pigs that were immunized ocularly with WRSS1, WRSS2, or WRSS3 and then challenged with the wild-type *S. sonnei* strain 53G, show comparable levels of immunogenicity and protective efficacy. Thus, deletion of the senA, senB, and the plasmid-borne msbB2 genes do not alter the protective immune responses induced with vaccine strains carrying a single virG(icsA) mutation. Furthermore, intragastric administration of the three vaccine candidates to Rhesus monkeys indicated that all three strains were excreted to the same extent, suggesting that genetic modifications that alter the level of lipid A acyl saturation do not reduce viability in an intestinal colonization model.

The *S. Sonnei* strain, Mosely, which is stable for the virulence phenotype, was used to construct the *Shigella* vaccine strains WRSS1, WRSS2, and WRSS3 (FIG. 1). The first generation vaccine strain (WRSS1) was constructed using a suicide vector as described in Hartman A B et al. 1998. WRSS2 and WRSS3 were constructed via a series of deletion mutations using λ-red recombineering as described in Ranallo et al 2007. Additional modifications to complete construction of WRSS2 include the loss of tetracycline resistance using fusaric acid. To create WRSS3, the msbB2 gene was deleted from WRSS2 and genomic PCR analysis was used to confirm all gene deletions. The strains were then characterized by HeLa cell invasion assay, colony immunoblotting, and the plaque assay as shown in FIG. 2.

Four groups consisting of ten guinea pigs were ocularly inoculated with $4\times10^8$ CFU of WRSS1, WRSS2, WRSS3, or normal saline as naïve control (see FIG. 3). Notably, additional experiments also indicated that the inoculation dose can be $5\times10^9$ without a deleterious effect (see FIG. 10). The immunizations were repeated on day 14 and, four weeks after the initial immunization, each guinea pig was challenged ocularly (Sereny test) with the wild-type *S. sonnei* strain 53G. Blood and mucosal secretions were collected as serum antibody responses (FIG. 4A) and mucosal antibody responses (FIG. 4B) from guinea pigs immunized with WRSS1, WRSS2, and WRSS3. Serum IgG-specific, serum IgA-specific, and mucosal IgA-specific immune responses against *S. sonnei* LPS and *S. sonnei* invasin-LPS complex (Invaplex) were measured by the ELISA assay. The IgG and IgA antibody responses were determined for day 0 (D0), day 14 (D14), and day 28 (D28) as well as two weeks after challenge (CLG). The geometric mean titer (GMT) of each group was calculated with 95% confidence intervals as indicated by error bars. No significant differences between WRSS1, WRSS2, and WRSS3 immune responses were detected by the one-way ANOVA test.

All guinea pigs were challenged with $1\times10^8$ CFU/eye of wild-type *S. sonnei* strain 53G 26 days after the final immunization (see FIG. 5). Guinea pigs (ten per group) were inoculated in the conjunctival sac and assayed for keratoconjunctivitis for 7 days. The reactions were scored as follows: 0, no inflammation or mild disease; 1, mild keratoconjunctivitis; 2, keratoconjuctivitis without purulence; and 3, severe keratoconjunctivitis with purulence. All guinea pigs immunized with the different vaccine strains (WRSS1, WRSS2, and WRSS3) were protected against keratoconjunctivitis.

Three groups of five monkeys were intragastrically inoculated with $4\times10^{10}$ CFU of WRSS1, WRSS2, and WRSS3, and then checked for clinical symptoms daily (see FIG. 6). Stool samples, blood drawing, rectal lavage, and proctoscopy were collected or performed as indicated.

Vaccine excretion in monkeys was detected by plating stool samples on Hektoen enteric agar plates (see FIG. 7). Colonies were checked for agglutination with *S. sonnei* antiserum (group D) and further identified by colony immunoblotting with anti-IpaB antibodies. The (+) sign represents culture positive stools and the (−) sign represents a negative culture or that no samples were collected (see FIG. 7). WRSS1, WRSS2, and WRSS3 were recovered from the stool of monkeys until about 5 to 7 days after immunization. No significant difference in excretion of vaccine was seen between the three groups.

TABLE 1

Serum IgA & IgG immune responses in monkeys after vaccination with *S. sonnei* vaccine strains

| | Animal | Serum IgA | | Serum IgG | |
|---|---|---|---|---|---|
| Vaccine | ID | LPS | Invaplex | LPS | Invaplex |
| WRSS1 | B34Z | − | + | − | + |
| | F942 | − | + | − | + |
| | JKA | − | + | − | + |
| | JPT | − | + | − | + |
| | TAB | − | + | − | + |
| WRSS2 | 20H | + | + | + | + |
| | 694Z | − | + | − | + |
| | 89-129 | − | − | − | + |
| | C42Z | − | + | + | + |
| | CJ2W | − | + | − | + |
| WRSS3 | 89-155 | − | + | − | + |
| | A14Z | − | − | − | − |
| | BVF | − | + | − | + |
| | J778 | + | + | − | + |
| | TAJ | − | − | − | + |

TABLE 2

Overall mucosal immune responses in monkeys after vaccination with *S. sonnei* vaccine strains

| | Animal | Fecal IgA | | ASC | |
|---|---|---|---|---|---|
| Vaccine | ID | LPS | Invaplex | LPS | Invaplex |
| WRSS1 | B34Z | − | + | − | + |
| | F942 | + | + | + | + |
| | JKA | − | + | − | + |
| | JPT | − | − | − | + |
| | TAB | − | + | + | + |
| WRSS2 | 20H | + | + | + | + |
| | 694Z | − | + | − | + |
| | 89-129 | − | − | − | − |
| | C42Z | + | + | − | + |
| | CJ2W | − | + | + | − |
| WRSS3 | 89-155 | − | + | − | − |
| | A14Z | − | − | − | − |
| | BVF | + | + | − | + |
| | J778 | − | + | + | + |
| | TAJ | − | − | + | + |

The *S. flexneri* 2a strain 2457T was used to construct the attenuated *Shigella* strains indicated in FIG. 8. The first generation vaccine strain SC602 (not shown) is similar to WRSf2G but is too reactogenic when given to human volunteers at doses greater than $10^4$ colony forming units. More attenuated strains (WRSf2G10-15) were constructed through a series of deletion mutations using λ red recombineering. Genomic PCR analysis was used to confirm all gene deletions. The strains were then characterized by HeLa cell invasion assay and colony immunoblotting (see FIG. 9).

Four groups consisting of eleven guinea pigs were ocularly inoculated with $5\times10^8$ CFU of SC602, WRSf2G12, WRSf2G15, or normal saline as naïve control (see FIG. 10). The immunizations were repeated on day 14 and, four weeks after the initial immunization, each guinea pig was challenged ocularly (Sereny test) with the wild-type *S. flexneri* strain 2457T. Blood and mucosal secretions were collected as serum antibody responses (FIG. 11A) and mucosal antibody responses (FIG. 11B) from guinea pigs immunized with SC602, WRSf2G12, WRSf2G15, or normal saline. Peak (Day 28) IgG-specific, serum IgA-specific, and mucosal IgA-specific immune responses against *S. flexneri* LPS and *S. flexneri* invasin-LPS complex (Invaplex) were measured by ELISA assay. The geometric mean titer (GMT) of each group was calculated with 95% confidence intervals as indicated by error bars. Equally significant, anti-LPS and anti-Invaplex IgG and IgA responses were detected in the serum of all vaccinated animals when compared to control groups. Equally significant anti-LPS mucosal IgA responses were detected in all vaccinated animals when compared to control groups. WRSf2G15 developed significantly higher anti-Invaplex responses when compared to both SC602 and WRSf2G12 as indicated by the asterisks in FIG. 11B.

Figure 12:
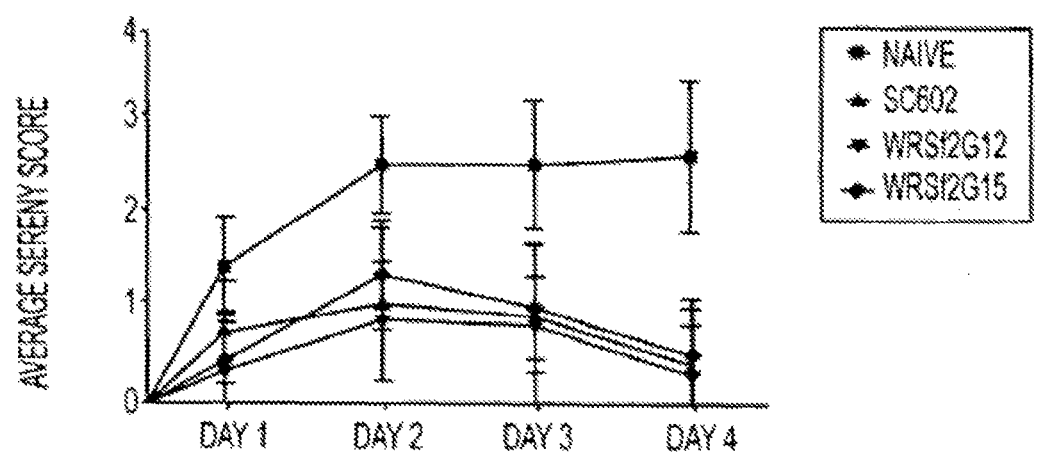
FIG. 12 shows the Protective efficacy of SC602, WRSf2G12, and WRSf2G15 following challenge with wild-type *S. flexneri* strain 2457T.

Each guinea pig was challenged with $1 \times 10^8$ CFU/eye of wild type *S. flexneri* strain 2457T 27 days after the final immunization (see FIG. 12). Guinea pigs were inoculated in the conjunctival sac and evaluated for keratoconjunctivitis for 4 days. The reactions were scored as follows: 0, no inflammation or mild disease; 1, mild keratoconjunctivitis; 2, keratoconjunctivitis without purulence; and 3, severe keratoconjunctivitis with purulence. All guinea pigs immunized with the different vaccine strains (SC602, WRSf2G12, and WRSf2G15) were protected against keratoconjunctivitis.

Evaluation of a bivalent mixture of live *Shigella* vaccines of two different serotypes occurred. The two new *S. flexneri* 2a vaccine candidates WRSf2G12 and WRSf2G15 were orally administered to groups of Rhesus monkeys either by themselves or in combination with the *S. sonnei* vaccine candidate WRSs3. Preliminary excretion data appears to indicate that the setAB genes deleted in WRSf2G12 and WRSf2G15 did not affect colonization of the gut, the msbB2 gene deleted in WRSf2G15 did not affect colonization of the gut, and that a bivalent mixture of a *S. sonnei* vaccine with a *S. flexneri* 2a vaccine having the combination of gene deletions did not affect the colonization of either strain. Since colonization of the gut is key to the generation of a protective immune response, these results indicate that a multivalent mixture of vaccine candidates of different serotypes, attenuated by a combination of gene deletions described in this patent application, can be administered to volunteers and be expected to be safe and elicit a protective immune response to each serotype. The possibility of combining these strains into a multivalent mix that can be given at one time and that would still be given at fairly low doses (in the range of $10^4$ to $10^6$ cfu) adds value to this patent application.

While various embodiments of the present invention have been described above, it should be understood that they have been presented by way of example only and not limitation. Thus, the breadth and scope of the present invention should not be limited by any of the above-described exemplary embodiments but should instead be defined only in accordance with the following claims and their equivalents.

What is claimed is:

1. A *Shigella* vaccine strain characterized as consisting of a gene deletion or gene inactivation of virG(icsA) in combination with senA(shET2) and senB(shET2-2) gene deletions or gene inactivations.

2. The *Shigella* vaccine of claim 1, wherein the strain is a virulent strain of 4 serogroups selected from *S. flexneri, S. sonnei, S. dysenteriae,* and *S. boydii.*

3. The *Shigella* vaccine strain of claim 2, wherein the strain is *S. flexneri* 2a.

4. The *Shigella* vaccine strain of claim 2, wherein the strain is *S. dysenteriae* 1.

5. The *Shigella* vaccine strain of claim 1, wherein the strain is further characterized by one or more traits selected from invasiveness of epithelial cells, lack of plaque formation in epithelial cell monolayers, or absence of keratoconjunctivitis in guinea pig eyes.

6. The *Shigella* vaccine strain of claim 1, wherein the strain is WRSS2 (ΔvirG, ΔsenA, ΔsenB).

7. The *Shigella* vaccine strain of claim 6, wherein the senA(shET2) and senB(shET2-2) genes are present on the large virulence plasmid.

8. An immunogenic composition comprising of one or more *Shigella* vaccine strains of claim 1 and a pharmaceutically acceptable carrier.

9. A vaccine comprising of one or more *Shigella* vaccine strains of claim 1 and a pharmaceutically acceptable carrier.

10. The vaccine of claim 9, wherein the vaccine is live and invasive.

11. A kit for treating a subject by inducing an immunoprotective response comprising of a container or containers with one or more of the *Shigella* vaccine strains of claim 1.

12. The kit of claim 11, wherein each container separately includes an individual *Shigella* vaccine strain.

13. A method comprising of administering an effective amount of one or more of the *Shigella* vaccine strains of claim 1 to a subject in need thereof, wherein the effective amount is a dose of $10^4$ to $10^6$ CFU.

14. The method of claim 13, wherein the effective amount is sufficient to induce a protective immune response against *Shigella* spp.

15. The method of claim 13, wherein one or more *Shigella* strains are orally administered.

16. The method of claim 15, wherein one or more *Shigella* strains are orally administered in a single dose.

* * * * *